United States Patent
Peter et al.

(10) Patent No.: US 6,359,612 B1
(45) Date of Patent: Mar. 19, 2002

(54) IMAGING SYSTEM FOR DISPLAYING IMAGE INFORMATION THAT HAS BEEN ACQUIRED BY MEANS OF A MEDICAL DIAGNOSTIC IMAGING DEVICE

(75) Inventors: Fritz Peter, Spardorf; Richard Hausmann, Erlangen, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/408,964

(22) Filed: Sep. 29, 1999

(30) Foreign Application Priority Data

Sep. 30, 1998  (DE) .......................................... 198 45 030

(51) Int. Cl.⁷ ................................................. G09G 5/00
(52) U.S. Cl. ..................................................... 345/156
(58) Field of Search ................................ 345/156, 179, 345/358; 434/367; 463/36; 382/288; 348/14, 18

(56) References Cited

U.S. PATENT DOCUMENTS

| | | | | |
|---|---|---|---|---|
| 4,843,568 A | * | 6/1989 | Krueger et al. | 364/518 |
| 5,528,263 A | * | 6/1996 | Platzker et al. | 345/156 |
| 5,988,851 A | | 11/1999 | Gent | 364/188 |
| 6,002,808 A | * | 12/1999 | Freeman | 382/288 |
| 6,175,610 B1 | * | 1/2001 | Peter | 378/8 |
| 6,176,782 B1 | * | 1/2001 | Lyons et al. | 463/36 |

FOREIGN PATENT DOCUMENTS

| DE | PS 196 12 949 | 8/1997 | ............ G06K/9/62 |
|---|---|---|---|
| DE | OS 197 08 240 | 9/1998 | ............ G06K/9/62 |

* cited by examiner

*Primary Examiner*—Amare Mengistu
(74) *Attorney, Agent, or Firm*—Schiff Hardin & Waite

(57) ABSTRACT

An imaging system for displaying image information that has been acquired by a medical diagnostic imaging device, has at least one projection surface, to which a projection device is allocated for purposes of reproducing image information on the projection surface. For controlling the reproduction of the image information, an optical detector detects gestures of an operator, and a control unit evaluates the output data of the detector for controlling the reproduction of the image information.

10 Claims, 3 Drawing Sheets

IMAGING SYSTEM FOR DISPLAYING IMAGE INFORMATION THAT HAS BEEN ACQUIRED BY MEANS OF A MEDICAL DIAGNOSTIC IMAGING DEVICE

BACKGROUND OF THE INVENTION

1. Field of the Invention

The present invention relates to an imaging system displaying imaging information that has been acquired by means of a medical diagnostic imaging device.

2. Description of the Prior Art

Imaging systems of the above general type serve in medical technology for displaying diagnostic imaging information obtained using different modalities ( medical diagnostic imaging devices) such as radiological CT devices, conventional radiology devices, MR devices, etc. Usually, the image information is transferred onto a transparent film, particularly an X-ray film, and is diagnosed at film viewing devices which are known per se, these being constructed in the fashion of light boxes. Images such as these represent a "frozen state"; that is, the characteristics of an image, such as contrast and the like, can no longer be influenced.

Adjustment of such characteristics is only possible when the observer does not view the image information at a film viewing device, but rather at a graphic workstation, such as are sold by Siemens AG under the names "MagicView" and "Prominence," since extensive possibilities for image processing are available with such units. Viewing of diagnostic image information at the monitors of such workstations, however, usually is outside of the typical work habits of the diagnosing physicians, who are used to making their diagnoses at a film viewing device and are not accustomed to working with computer and mouse.

Displaying of image information on a projection surface by means of a video projector, instead of by means of a transparent film and a film viewing device or by means of a monitor, is known.

Operating devices on the basis of input interfaces known as virtual touchscreens (SIVIT-Siemens Virtual Touchscreen) is also known. Here, a video projector projects operating elements onto a projection surface. Movement of a finger on the projection surface, which is illuminated with an infrared lamp, is picked up by an infrared-sensitive video camera, and is interpreted like movement with a mouse; the lingering of the finger at a specific position being recognized as the equivalent of a mouse click. A further simplification of the operating procedures is possible by means of an additional evaluation of the gestures of the operator. Such virtual touchscreens are described in German PS 196 12 949 and German OS 197 08 240.

SUMMARY OF THE INVENTION

It is an object of the present invention to provide an imaging system of the general type described initially, wherein even an operator who is unaccustomed to working with a graphic workstation can influence the reproduction of the image information.

The above object is achieved in accordance with the principles of the present invention in an imaging system for displaying image information acquired using a medical diagnostic imaging device, the system having at least one projection surface and a projection device which reproduces the image information on the projection surface, and an optical detector which detects gestures of an operator or which detects the position of a pointing element held by an operator, and a control unit which evaluates output data from the optical detector to generate control signals based on the output data for controlling the reproduction of the image information by the projection device.

In the imaging system of the invention, because the image information is not displayed on a monitor, but rather on a projection surface, the operator is given a perspective that corresponds to that when working with a film viewing device. As a result of the evaluation of the gestures of the operating person, he or she is able to influence the reproduction of the image information without having to work at a computer or a graphic workstation or having to be familiar with such workstations.

Accordingly, a virtual touchscreen is employed, having operating elements which are activated by a hand, preferably a finger, of an operator, with the aid of a pointer or of a light pointer as a pointing element, for example.

According to a preferred embodiment of the invention, the control unit contains an image processing stage, and the control unit evaluates the output data of the detector for controlling the image processing stage. With a suitable design of the image processing stage, it is then possible to control by gesture all the image processing steps which are otherwise common with mouse control, such as windowing, dimensioning of objects, 3D functions, etc.

In another version of the invention, the control unit contains circuitry for mixing different image information, making it possible to operate complex functions such as image fusion, that is, the mixing of image information originating in different modalities. For example, it is possible in image fusion to a virtual endoscopy display, such as can be calculated on the basis of three-dimensional image data acquired by means of a radiological CT device, with the image information acquired in a real endoscopic examination of the corresponding body region.

Furthermore, the control device can have the capability of retrieving different image information, so that it is possible to display and process random images that are stored in the imaging system or archived externally. The control unit can contain speech recognition circuitry for detecting the speech of an operator, and the control unit can evaluate the output data of the recognition circuitry speech either for controlling the imaging system or for creating and storing alphanumeric comments, which are allocated to the displayed image information. It is also possible to execute other operating actions using voice control, or to dictate a diagnosis of the image information directly, as is taught in "Diktieren auf das Papier" (Elektronik 16/1997, p. 47).

In order to guarantee the necessary security, or to prevent misuse, the means for detecting speech recognition circuit can contain voice recognition capability, so that commands or dictation are only recognized if they are spoken by an authorized person.

DESCRIPTION OF THE PREFERRED EMBODIMENTS

Figure 1:
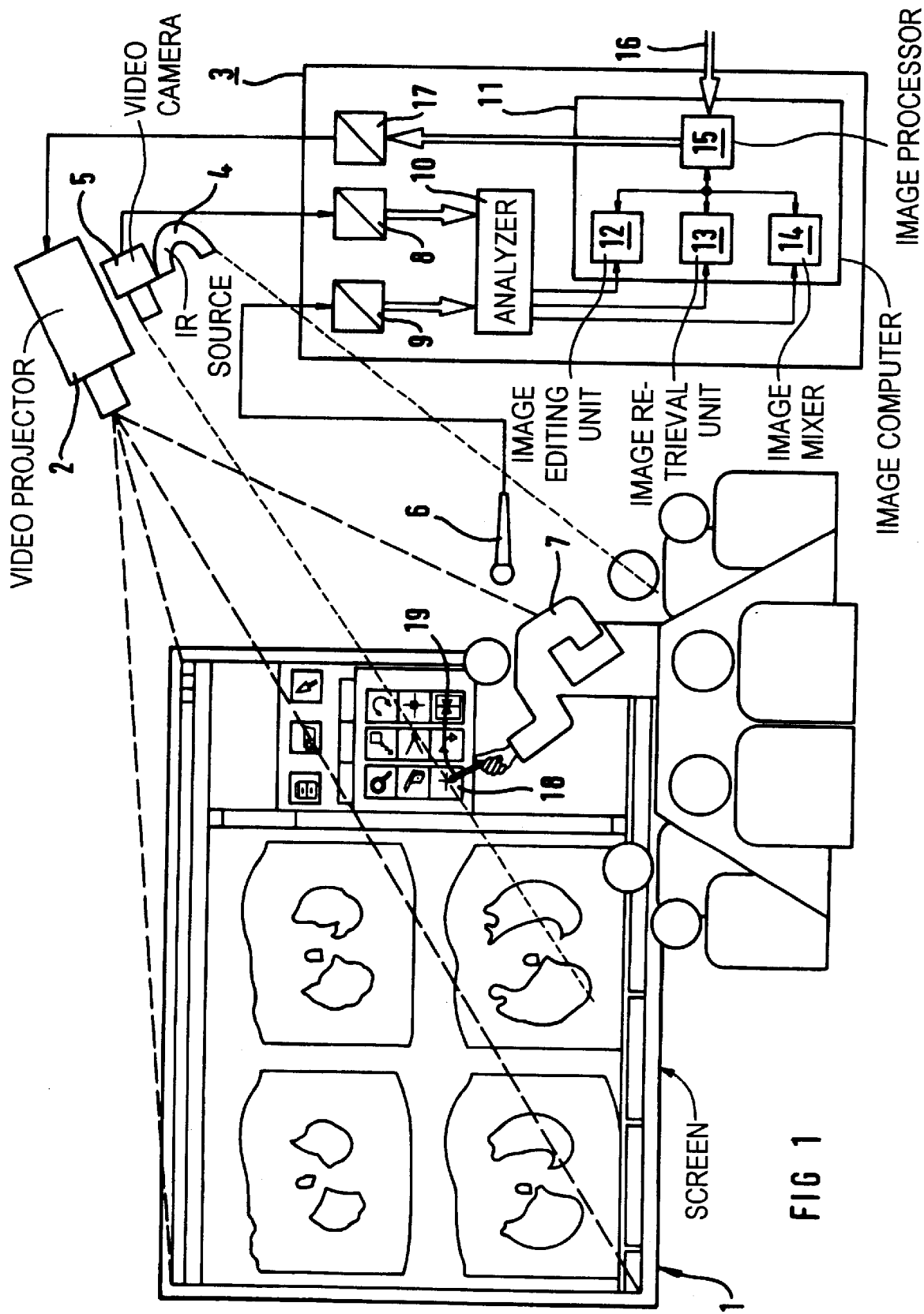
FIG. 1 is schematic block diagram of an inventive imaging system.

The imaging system according to FIG. 1 serves for purposes of displaying image information, acquired by means of a medical diagnostic imaging device (modality), on a projection surface, which is a screen 1 in FIG. 1. FIG. 1 as an example shows tomograms of four different slices of the chest region of a patient which have been acquired with a radiological CT device.

The display occurs by means of a projection device, namely a video projector 2, which receives the signals that correspond to the images to be displayed from a control unit 3.

A video camera 5, which serves as a detector for operator-produced command movements and/or gestures, and a microphone 6 are also connected to the control unit 3.

In order to avoid malfunctions, the video camera 5 is not sensitive to ambient light, but only to a defined light spectrum, which necessitates an illumination of the projection surface which is to be monitored using a corresponding light source, so that the video camera 12 can recognize the finger, for example, of the operator. In the case of the exemplary embodiment described herein, a video camera 5 is used which is only sensitive to infrared light, an infrared light source 4 being allocated thereto.

The video camera 5 and the infrared light source 4 are oriented to a region in space in which an operator is located. It is thus possible to pick up the operator with the video camera 5 without interference from ambient light. The corresponding signals of the video camera 5 are analyzed by the control unit 3 as to whether the operating person 7 is making typical gestures which are allocated to specific operating steps related to the reproduction of image information on the screen 1. When the control unit 3 recognizes a typical gesture of this sort from the output signals of the video camera 5, it executes the corresponding operating step.

The control unit 3 also analyzes the output signals of the microphone 6 to determine whether the operator 7 is giving typical oral, verbal commands to which specific operating steps are allocated. When the control unit 3 recognizes a typical oral, verbal command of this sort from the aid of the output signals of the microphone 6, it executes the corresponding operating step.

As can be seen in FIG. 1, the control unit 3 contains two analog/digital converters 8,9, to which the output signals of the video camera 5 and the microphone 6 are fed, respectively. The digital data corresponding to these output signals proceed to an analyzer 10.

As is also shown from FIG. 1, the control unit 3 contains an image computer 11, which receives commands from the analyzer 10.

For executing these commands, the image computer 11 contains an image editing unit 12, an image retrieving unit 13, an image mixer 14, and an image processor 15.

These components can be separately present as such, although the control unit 3, the analyzer 10 and the image computer 11 are preferably realized together in the form of a correspondingly programmed universal computer, such as a PC.

The analyzer 10 analyzes the data that correspond to the output signals of the video camera 5 and the microphone 6 to determine whether the operator 7 is currently performing a typical gesture corresponding to an operating step, or is giving a typical oral command corresponding to an operating step. If this is the case, the analyzer 10 delivers corresponding control data to the image editing unit 12 and/or to the image retrieving unit 13 and/or to the image mixer 14, which execute the corresponding operating step in conjunction with the image processor 15.

For achieving the described function, pixel patterns corresponding to the typical gestures are stored in the analyzer 10 in digital form, along with the corresponding operating steps, as well as waveforms corresponding to typical oral commands. The analyzer 10 compares the digitized output signals of the video camera 5 and the microphone 6 to the stored pixel patterns or waveforms, respectively. When the analyzer 10 detects a pixel pattern that corresponds to a typical gesture, or a waveform that corresponds to a typical oral command, in the respective output signals of the video camera 5 or the microphone 6, the analyzer 10 activates the image editing unit 12 and/or the image retrieving unit 13 and/or the image mixer 14 as described for purposes of executing the corresponding operating step.

As can be seen in FIG. 1, in addition to the tomograms, operating fields can be displayed (arranged to the right of the four tomograms in FIG. 1), as on the monitor of a graphic workstation. The operating fields can respectively contain icons such as are commonly used at graphic user interfaces of workstations, one of which is referenced 18.

In the exemplary embodiment, the image information displayed on the screen 1 corresponds exactly to the image information appearing on the screen surface of the monitor of a graphic workstation.

As described below, in the inventive imaging system, the operator is able to interactively perform image processing operations with reference to the projected tomograms using these projected operating elements.

The video camera 5 covers at least that region of the screen 1 on which the display of operating elements ensues, this region also being illuminated by the infrared light source 4. When an operator moves a hand—preferably a finger or as indicated in FIG. 1, a pointer 19—on the screen 1, then the movement of the finger or the pointer 19 is interpreted like the movement of a mouse in a graphic workstation. A lingering of the finger or the pointer 19 on a specific position of the screen 1 over a definite time period, for instance one-half second, is interpreted as a mouse click. It is thus clear that an operator can operate image processing interactively, as it were, by means of his or her finger, or pointer 19. A virtual touchscreen, as it were, thus is realized by the screen 1, the video projector 2, the video camera 5 and the infrared light source 4.

The analyzer 10 also analyzes the data that correspond to the output signals of the video camera 5 as to whether an operator is currently activating one of the icons projected on the screen 1 using a finger or the pointer 19. When this is the case, the analyzer 10 forwards corresponding data to the image editing unit 12 and/or to the image retrieving unit 13 and/or to the image mixer 14, which perform the corresponding operating step in conjunction with the image processor 15.

Instead of using a finger or a pointer, the activation of an icon can also occur using a light pointer which emits light in the of sensitivity range of the video camera 5 and which is directed toward the icon to be activated.

The operating steps performed by the image editing unit 12 involve contrast changes, which may relate to a displayed image in its entirety or only to subregions, or involve the enlargement factor with which an image is displayed, etc.

The operating steps performed the image retrieving unit 13 involve the retrieval of image information—that is a specific, image, a specific series of images or specific individual images from an external archive, from a modality, or from a mass memory belonging to the imaging system—and the display thereof. The signals corresponding to the image information to be displayed on the screen 1 are fed to the image computer 11 via a line 16, in the form of digital signals in the exemplary embodiment.

The operating steps performed by the image mixer 14 concern the mixing of image information and the display of the mixed image information, whereby the image information to be mixed can be obtained from various examinations, or various examination portions, and/or from various modalities.

In order to be able to display the image information that has been acted on by the image computer 11 according to the commands given by the operator 7 on the screen 1 using the video projector 2, the control unit 3 contains a digital/analog converter 17, which converts the digital data delivered by the image processor 15 of the image computer 11 into an analog video signal, which is fed to the video projector 2.

Examples of gestures which the system is capable of understanding are illustrated in FIGS. 2 to 7.

Figure 2:
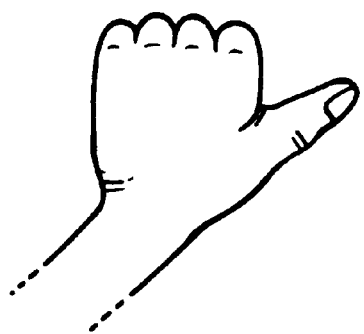
FIGS. 2 to 7 respectively show examples of various gestures which the imaging system of FIG. 1 is capable of recognizing.
Figure 3:
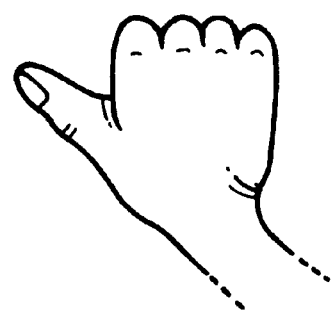

Here, given the recognition of the gesture illustrated in FIG. 2, the next image is displayed, whereas given the recognition of the gesture illustrated in FIG. 3, the previous image is displayed.

Figure 4:
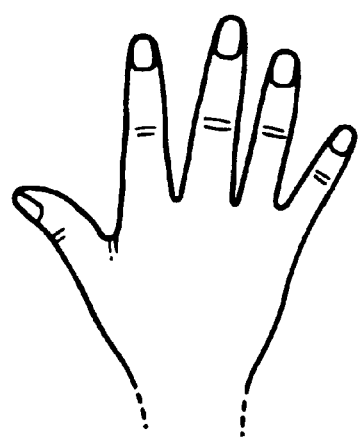
Figure 5:
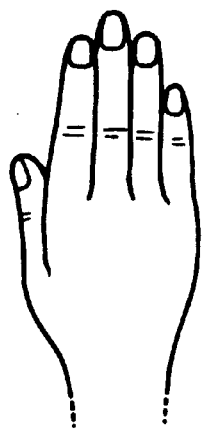
Figure 6:
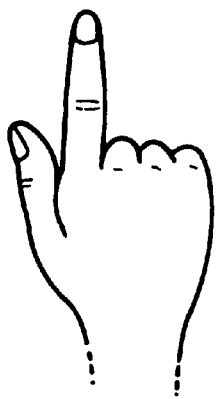
Figure 7:

Given the recognition of the gesture illustrated in FIG. 4, the contrast of the image currently being displayed is increased, whereas the contrast of the displayed image is reduced given the recognition Of the gesture of FIG. 5. Given the detection of the gesture according to FIG. 6, one of two items of image information that are blended together is shifted up relative to the other, while given the detection of the gesture in drawing 7, a downward shift occurs.

It is thus possible to initiate by gesture a variety of operating steps which are required in connection with the reproduction of image information.

The nature of the operating elements which are projected in the case of the exemplary embodiment is only an example.

The nature of the other information that is displayed on the screen in the present exemplary embodiment is also only exemplary.

The gestures described in the present embodiment which are evaluated for purposes of the operation are likewise only.

The projection surface need not necessarily be constructed as a screen, as in the case of the exemplary embodiment. Other, preferably smooth, flat surfaces can also be used as the projection surface.

The basic advantages of the inventive imaging system are summarized below, demonstrating the utility of the invention to the user.

The user, e.g. a radiologist, need not deviate from his or her customary manner of working at the film viewing device, and in spite of this can perform additional interactive image processing steps which improve his or her diagnosis and also permit more functions. A time savings in diagnoses can be achieved in this way.

3-D functions such as "virtual endoscopy" can be easily realized clearly and ergonomically, and they offer a new possibility for spatial diagnoses.

Image diagonals of up to 61 micro-inches can already be realized with video beamers, so that an appreciably larger image display is possible than using the 21-micro-inch monitors common until now. In the future, further improvements can be expected of the image size that can be achieved with video projectors.

The angular field in the image display using video projectors is appreciable larger than for a monitor; that is, even a side viewing position offers excellent image recognizability.

The display using a video projector is also richer in contrast than in film viewing devices and conventional monitors, even given unfavorable light relations.

Inventive imaging systems are considerably more economical than known imaging systems with high-resolution monitors and thus offer appreciable cost saving potential in construction and in production.

Inventive imaging systems are particularly suitable for filminess clinics with electronic, particularly digital image archives.

Inventive imaging systems are particularly suitable for radiological conferences, over the Internet as well.

Inventive imaging systems are suitable for public presentations, as indicated in FIG. 1.

Inventive imaging systems function just as well when the patient's chart is used as projection surface, and information or patient images can be retrieved in an operation and/or in a patent examination by gesture recognition.

Although modifications and changes may be suggested by those skilled in the art, it is the intention of the inventor to embody within the patent warranted hereon all changes and modifications as reasonably and properly come within the scope of their contribution to the art.

We claim as our invention:

1. An imaging system for displaying image information acquired using a medical diagnostic imaging device, said imaging system comprising:

a projection surface;

a projection device having a field of view directed at said projection surface for reproducing medical diagnostic image information in a first area on said projection surface and for reproducing operating fields in a second area on said projection surface separate from said first area, said operating fields having respective operating functions allocated thereto which alter said reproduction of said image information;

a hand held pointer;

an optical detector having a field of view encompassing an operator holding said pointer, said optical detector detecting movement and positioning of said pointer by said operator over said operating fields and generating output data dependent on said movement and positioning of said pointer; and a control unit supplied with said output data for controlling reproduction of said image information by said projection device dependent on said movement and positioning of said pointer over said operating fields.

2. An imaging system as claimed in claim 1 wherein said control unit includes an image editing unit, and wherein said control unit controls said image editing unit dependent on said output data.

3. An imaging system as claimed in claim 1 wherein said control unit includes an image retrieval unit, and wherein said control unit controls said image retrieval unit dependent on said output data.

4. An imaging system as claimed in claim 1 wherein said control unit includes an image mixing unit, and wherein said control unit controls said image mixing unit dependent on said output data.

5. An imaging system as claimed in claim 1 wherein said control unit includes a speech recognition circuit for detecting speech by said operator, said speech recognition circuit generating speech-dependent output data, and wherein said control unit evaluates said speech-dependent output data and additionally controls said projection device according to said speech-dependent output data.

6. An imaging system as claimed in claim 5 wherein said control unit comprising means for producing and storing alphanumeric representations of said speech-dependent output data allocated to the medical diagnostic image information displayed on said projection screen by said projection device.

7. An imaging system as claimed in claim 5 wherein said control unit comprises a voice recognition circuit for identifying the voice of said operator.

8. An imaging system as claimed in claim 1 wherein said projection device reproduces said operating fields with respective operating field images corresponding to standardized computer image control icons.

9. An imaging system as claimed in claim 8 wherein said control unit interprets said output data to control said reproduction of said image information by correlating said movement and said positioning of said pointer to operation of a computer mouse.

10. An imaging system as claimed in claim 9 wherein said control unit interprets a pause over a selected one of said operating fields for a predetermined time duration as a simulation of a mouse click of said computer mouse.

* * * * *